United States Patent [19]

Boschetti

[11] Patent Number: 4,497,317

[45] Date of Patent: Feb. 5, 1985

[54] VAGINAL DEVICE FOR CONTRACEPTIVE CONTROL

[76] Inventor: Enrica Boschetti, Via Melchiorre Gioia, 171, 20125 Milano, Italy

[21] Appl. No.: 443,744

[22] Filed: Nov. 22, 1982

[30] Foreign Application Priority Data

Dec. 9, 1981 [IT] Italy .................. 25486 A/81

[51] Int. Cl.³ ............................................. A61F 5/46
[52] U.S. Cl. ................................................ 128/127
[58] Field of Search ................................... 128/127

[56] References Cited

U.S. PATENT DOCUMENTS

| 3,117,573 | 1/1964 | Snell | 128/127 |
| 3,169,894 | 2/1965 | Monett | 128/127 X |
| 3,216,422 | 11/1965 | Steiger et al. | 128/127 X |
| 4,261,352 | 4/1981 | Sedlacek | 128/127 |
| 4,311,543 | 1/1982 | Strickman et al. | 128/127 |

Primary Examiner—John D. Yasko
Attorney, Agent, or Firm—Michael J. Striker

[57] ABSTRACT

A contraceptive vaginal or intra-uterine device is formed of two separate elements one of which is a ring and a second is a container made of fabric impregnated with a spermicide or medicinal substance. The ring before use is inserted into the container through a closable opening formed therein. An additional closable opening is formed in the container for removing the ring from the container.

14 Claims, 4 Drawing Figures

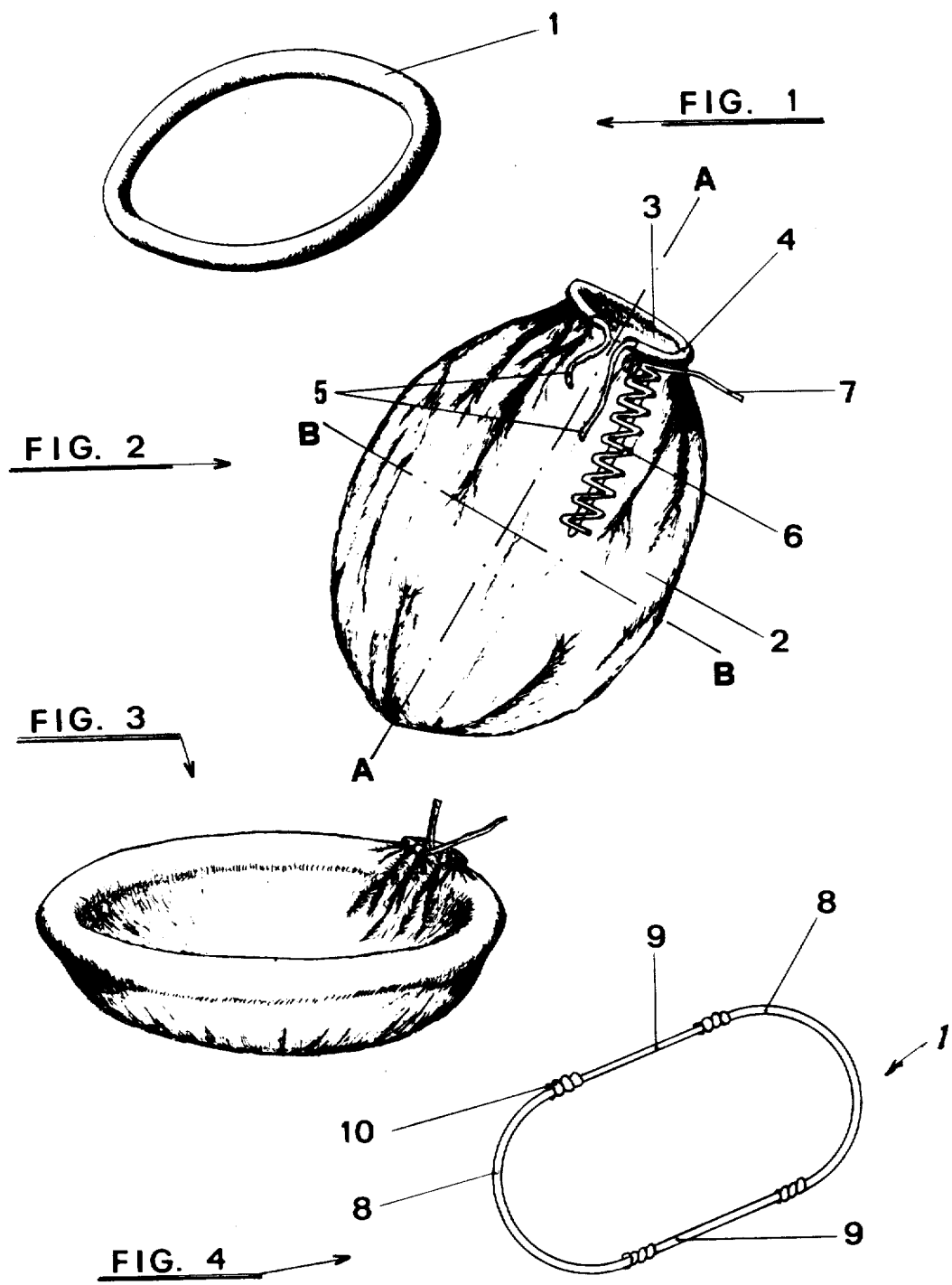

VAGINAL DEVICE FOR CONTRACEPTIVE CONTROL

BACKGROUND OF THE INVENTION

The present invention relates to intra-uterine contraceptive devices.

None-chemical contraceptive means generally known as diaphragms are known in the prior art. Such diaphragms are normally associated immediately before being used, with spermicide and/or medicinal substances. Generally such diaphragms comprise an outer structure which is a rubber cap peripherally fixed to a base structure. These diaphragms are of circular or oval shape and the outer structure is generally planar. Moreover, the outer structure which is elastic may be peripheraly deformed by a user or a therapist to anatomically adapt its shape.

Known vaginal diaphragms are disclosed, for example in U.S. Pat. Nos. 961,880; 2,087,610; 2,443,943; 2,463,356; 2,529,363; 2,638,896; 2,664,082; 2,679,589; 2,823,669; 3,169,894; 2,875,755; 3,060,931; 4,031,886 and the German Pat. No. 557,914.

The contraceptive diaphragm disclosed in U.S. Pat. No. 2,443,943 to T. Young includes an outer structure formed of two separate steel segments housed in a spiral spring incorporated in a rubber sleeve.

The diaphragm is disclosed in U.S. Pat. No. 2,463,356 to J. T. Clark, in which the oval outer structure is a rubber sleeve accommodating two flat springs each having its ends juxtaposed to the corresponding ends of another spring to provide for an adjustable diaphragm.

The diaphragm disclosed in U.S. Pat. No. 2,823,669 to E. Kunnas is of a circular shape and comprises an outer structure in which two separate steel segments are connected to each other by two small spiral springs, wherein their pointed ends are engaged, all these elements being housed within a larger closed spiral spring which in turn is positioned in a rubber sleeve, so as to provide a diaphragm that may be folded for introduction in the anatomic cavity.

Applicant has suggested a number of model and patent applications concerning, respectively a circular or oval diaphragm in which the cap is connected with the outer structure in accordance with the middle plane of the outer structure, an oval diaphragm in which the inner armour of the outer structure may be extended or shortened in order to modify the dimensions of the diaphragm, a diaphragm whose outer structure comprises a spiral spring incorporating flexible metal bars and is of oval or elliptic cross-section with a main axis substantially parallel to an axis perpendicular to the diaphragm plane.

A pessary disclosed in U.S. Pat. No. 4,031,886 to Morhenn is formed by an outer structure having a specific shape for receiving the human cervix and a bag adapted to receive that outer structure. The bag has two generally planar walls each having four edges and may be impregnated with medicaments.

The inconvenience with known diaphragms, however is that they should be used in association with spermicide and/or medicinal substances to be applied before use and require the availability of a diaphragm and of a container for those substances, which involves practical, psychological and financial problems.

Furthermore, the handling of a gummy material which becomes slimy due to the applied substancies is also inconvenient.

Moreover, the staying of one of such substances on a rubber cap may be uncertain and a source of unpleasant surprises.

In the pessary disclosed in U.S. Pat. No. 4,031,886 the outer structure must be oriented in a unique way in order to be introduced into the bag; the pessary must be applied into the anatonic cavity in a unique direction; the shape of the outer structure can be only adapted to work as a pessary and the outer structure does not allow for adjustments to the shape and dimensions—all the above cause difficulties in use of the disclosed pessary.

SUMMARY OF THE INVENTION

It is an object of the invention to provide an improved vaginal device for contraceptive control.

It is another object of the invention to provide a non-chemical contraceptive device, which is reliable.

These and other objects of the invention are attained by a contraceptive vaginal device comprising an elastic ring of a generally circular shape having a general plane; and a hollow elastic container made of expandable fabric and having walls impregnated with a spermicide or contraceptive medicinal substance, said ring being insertable into said container to stretch its walls and to shape it into a vaginal barrier. The spermicide and/or medicinal substance is applied to the inner and outer surfaces of the container.

According to a further feature of the invention the ring may include an outer sleeve of elastic material and an inner spring-like means inserted into said outer sleeve for allowing the peripheral dimensions and the shape of the outer sleeve to be modified by an external force applied thereonto.

The container may be of a substantially ellipsoid shape, said container being formed with a first opening for receiving said ring and means for closing said opening after said ring has been inserted into the container.

The container of the elipse-like or elipsoid shape may have a larger axis and a smaller axis, said container being adapted to receive said ring with its general plane lying along said larger axis or along said smaller axis whereby the container and the ring are geometrically adjustable to each other and form in assembly said vaginal barrier of a cup-like shape having a periphery substantially coinciding with the periphery of the ring so that two walls of the container are superpositioned one on another and are kept close to each other also due to the adherence between the layers of the medicament applied to the opposite surfaces.

According to a still further modification of the invention the container may be provided with a tubular collar extended along the first opening, said closing means being a yarn received in said tubular collar, said yarn having free ends which are pulled and knotted by a user to close the first opening after the ring has been inserted into the container.

The container may be formed with a second elongated opening, said second opening being closed with a basting adapted to be easily and rapidly removed by a user to draw the ring out from the container through the second opening.

Alternatively, the container may be of cotton, plastic material, natural or synthetic rubber, natural or synthetic sponge. The advantages of the invention are as follows: the container made of fabric impregnated with a medicament is easy to use, is very safe and prevents from using large quantity of medicaments (for instance, of active substance) that may prove to be dangerous to the vaginal mucosa; the stable localization of the medicament on and in the container walls makes sure the effect thereof during several hours; the handling of a container made of fabric rather than of a gummy is more convenient and this result is increased because the container is already impregnated, which prevents one from the duty to spread medicament on the cap of a diaphragm before using; the same ring may be used for years without the need to replace it in the case of changes in the anatomic dimensions and form, whereas the container may be thrown away, if desired, even after one single sexual intercourse; thus the economic advantage of the invention seems to be evident.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

The ring may include an outer sleeve of natural rubber or equivalent synthetic material into which means are incorporated for allowing the peripheral dimensions of the outer sleeve to be modified to give the ring the desired shape.

BRIEF DESCRIPTION OF THE DRAWINGS

FIG. 1 is a perspective view of a ring;

FIG. 2 is a perspective view of a container for receiving the ring of FIG. 1;

FIG. 3 is a perspective view of the assembled vaginal device according to the invention; and FIG. 4 is a perspective view of the ring according to another embodiment of the invention.

DETAILED DESCRIPTION OF THE PREFERRED EMBODIMENTS

Referring now to the drawings and first to FIG. 1, a ring 1 is shown which may be circular or oval. The ring of the known structure can be utilized in the vaginal device according to the invention, for example the ring shown in U.S. Pat. No. 2,823,669 to Kunnas, which ring includes two separate segments made out of steel rod and connected to each other by means of two small spiral rings, the connected segments being then incorporated into a larger closed spiral spring which in turn is placed into a rubber sleeve housing the assembly. It is, of course, understood then any suitable elastic material, natural or synthetic may be used for the sleeve of the ring.

FIG. 2 illustrates a container 2 which is a bag, made, preferably of cotton or another soft and absorbent material. Container 2 may be also produced of any suitable flexible plastic material, such as synthetic or natural rubber or natural or synthetic sponge. Container 2 is formed with a first substantially circular opening 3 into which ring 1 is to be introduced. A tubular housing 4 is provided around the opening 3 for accommodating therein a yarn 5 passing through the housing 4 and having its ends extended outwardly of the tubular housing whereby a user can pull those ends and knot them, after the ring 1 has been inserted into the container, to close the opening 3. A second elongated opening 12 is provided in the peripheral wall of the container. The edges of opening 12 are closed by a yarn or basting 6. The length of opening 12 may be of several centimeters. When a free end 7 of the yarn 6 is pulled out from the wall of the container aperture 12 is released and ring 1 can be easily and rapidly removed from container 2. Container 2 has substantially a shape of an ellipsoid if it is three-dimensional as in FIG. 2, or of an ellipse if considered flat.

A spermicide and/or medicinal substance is applied to the outer and inner surfaces of the container whereby the container is impregnated with medicament, this preventing one from using large quantity of medicaments.

It is understood that the ring 1, which is always an elastic structure, is conveniently folded by the fingers of a user for introduction into the container 2 through opening 3. Once the ring 1 is inserted into the container 2, it takes again its natural shape or the shape previously imparted by a user or a therapist by conveniently deforming the inner means provided in the ring for this purpose and the ring stretches the container walls to form a vaginal barrier, as illustrated in FIG. 3. The container walls are cup-shaped and positioned one on the other. According to FIG. 3, the ring 1 is placed into the container 2 with its plane lying in the main axis A-A of the container shown in FIG. 2, but alternatively the ring 1 may be placed into the container 2 with its plane lying in the minor axis B-B of the container shown in FIG. 2.

It is to be understood that the ring which is introduced into the container to shape the latter into the vaginal device may be alternatively formed by a closed spiral ring or by a steel solid ring or by a rubber ring formed around a core of steel or another material of similar elastic properties. One of the modifications of the ring is shown in FIG. 4. The ring 1 depicted in FIG. 4 is formed of two small steel arcs 8 connected to each other through elastic steel bars 9 by means of four articulated joints each made by engaging two opposed ends of the respective arc and the respective bar into a helical spring 10. The opposed ends of the arc 8 and bar 9 contacting each other within the spring 10 are connected to each other by any suitable means. The ring of the described structure is elastic and may be folded by the fingers of a user to be inserted into opening 3 of container 2.

It will be understood that each of the elements described above, or two or more together, may also find a useful application in other types of vaginal contraceptive devices differing from the types described above.

While the invention has been illustrated and described as embodied in a vaginal contraceptive device, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A contraceptive vaginal device comprising a substantially elastic ring of a generally circular shape and having a general plane; and a hollow elastic container made of expandable fabric and having walls impregnated with a spermicide or contraceptive medicinal substance, said ring being insertable into said container to stretch its walls and to shape it into a vaginal barrier, said container being of a substantially ellipsoid shape and being formed with a first opening for receiving said ring and including means for closing said opening after said ring has been inserted into said container, said container having a larger axis and a smaller axis and being adapted to receive said ring with its general plane lying along said larger axis or along said smaller axis, whereby said container and said ring are geometrically adjustable to each other and form in assembly said vaginal barrier of a cup-like shape having a periphery substantially coinciding with the periphery of said ring so that two walls of said container are superpositioned one on another, said container being provided with a tubular collar extended along said first opening, said closing means being a yarn received in said tubular collar, said yarn having free ends which are pulled and knotted by a user to close said first opening after said ring has been inserted into said container.

2. The device as defined in claim 1, wherein said ring is round.

3. The device as defined in claim 1, wherein said ring is oval.

4. The device as defined in claim 1, wherein said ring is a known per se ring similar to the ring utilized in contraceptive diaphragms.

5. The device as defined in claim 1, wherein said ring includes an outer sleeve of elastic material and an inner spring-like means inserted into said outer sleeve for allowing the peripheral dimensions and the shape of the outer sleeve to be modified by an external force applied thereonto.

6. The device as defined in claim 1, wherein said container is formed with a second elongated opening, said second opening being closed with a means adapted to be easily and rapidly removed by a user to draw said ring out from said container through said second opening.

7. The device as defined in claim 6, wherein said means is a basting closing said second opening.

8. The device as defined in claim 1, wherein said container is formed of cotton fabric.

9. The device as defined in claim 1, wherein said container is formed of natural rubber.

10. The device as defined in claim 1, wherein said container is formed of synthetic rubber.

11. The device as defined in claim 1, wherein said container is formed of natural sponge.

12. The device as defined in claim 1, wherein said container is formed of synthetic sponge.

13. The device as defined in claim 1, wherein said ring includes two arcs of steel diametrically opposed each other, two intermediate rods of steel extended between the free ends of said opposed arcs and four helical springs receiving the free ends of the arcs and the intermediate rods for connecting them to each other.

14. The device as defined in claim 5, wherein said outer sleeve is made of rubber.

* * * * *